United States Patent [19]

Uphues et al.

[11] Patent Number: 4,874,883
[45] Date of Patent: Oct. 17, 1989

[54] PROCESS FOR THE PRODUCTION AND ISOLATION OF MONOALKYL PHOSPHORIC ACID ESTERS

[75] Inventors: Guenter Uphues, Monheim; Uwe Ploog, Haan; Klaudia Bischof, Werne, all of Fed. Rep. of Germany

[73] Assignee: Henkel Kommanditgesellschaft auf Aktien, Duesseldorf, Fed. Rep. of Germany

[21] Appl. No.: 150,691

[22] Filed: Jan. 29, 1988

[30] Foreign Application Priority Data

Jan. 30, 1987 [DE] Fed. Rep. of Germany ....... 3702766

[51] Int. Cl.$^4$ ............................................. C07F 9/09
[52] U.S. Cl. .................................... 558/150; 558/110
[58] Field of Search ..................... 558/110, 111, 150

[56] References Cited

U.S. PATENT DOCUMENTS 4,670,575  6/1987  Kurosaki et al. ................... 558/110

FOREIGN PATENT DOCUMENTS 1475109  6/1977  United Kingdom .

OTHER PUBLICATIONS

Journal of the American Oil Chem., Soc., 55, 839, (1979).

Primary Examiner—Anton H. Sutto
Attorney, Agent, or Firm—Wayne C. Jaeschke; Henry E. Millson, Jr.; John E. Drach

[57] ABSTRACT

In the production of monoalkylphosphoric acid esters, at least one fatty alcohol or mixtures of fatty alcohols containing from 8 to 18 carbon atoms and preferably from 12 to 14 carbon atoms in a straight chain is/are reacted with a 0.2 to 2 molar excess of polyphosphoric acid at a temperature of 60° to 130° C.; following an after-reaction time of 120 to 300 minutes at a temperature of 95° to 105° C., the product of this reaction is slowly hydrolyzed at 90° to 100° C. with 0.5 to 1.0 mole water, based on the quantity of phosphorus atoms in the reaction mixture, the hydrolysis product is neutralized to a level of from 40 to 65% and preferably to a level of from 50 to 60%, based onthe acid number, with dilute alkali metal hydroxide, and the two phases formed are separated from one another after a residence time of 30 to 180 minutes at a temperature in the range of from 50° to 95° C.

10 Claims, No Drawings

PROCESS FOR THE PRODUCTION AND ISOLATION OF MONOALKYL PHOSPHORIC ACID ESTERS

BACKGROUND OF THE INVENTION

1. Field of the Invention:

This invention relates to the reaction of long-chain fatty alcohols with polyphosphoric acid to form monoalkylphosphoric acid esters and to their separation from the orthophosphoric acid formed during the reaction.

2. Statement of Related Art:

Monoalkylphosphoric acid esters (monoalkylphosphates) are industrially produced by reaction of alcohols with phosphorus oxychloride. G. Imokawa "Journal of the American Oil Chemists' Society", 55, 839 (1979) describes a corresponding solvent-free reaction. On completion of the reaction, excess phosphorus oxychloride is hydrolyzed by addition of water and the phosphoric acid formed is separated off by ether/water extraction.

British patent 1,475,109 describes a process for the reaction of alcohols with phosphorus oxychloride in a ration of 1.1 moles of phosphorus oxychloride per mole of starting material (alcohol), the reaction being carried out in the presence of cycloalkanes and/or alkanes as solvent. This known process is carried out in dilute solutions. Due to the quantity of hydrogen chloride released during the reaction (3 moles/monoalkylphosphate), the process has to satisfy particular technological requirements. According to GB 1,475,109, the presence of solvents is necessary to avoid secondary reactions, such as for example the formation of diesters. Accordingly, the reaction to produce monoalkylphosphates is carried out in a very large quantity of cyclohexane.

According to Ullmanns Encycklopadie der technischen Chemie, 4th Edition, Vol. 18, page 389, monophosphoric acid esters are formed in addition to free phosphoric acid in the reaction of the alcohols with polyphosphoric acid. The phosphoric acid formed during the reaction is particularly troublesome in cosmetic products, electrolyte solutions, emulsions, and also in the spinning of synthetic fibers.

DESCRIPTION OF THE INVENTION

Other than in the operating examples, or where otherwise indicated, all numbers expressing quantities of ingredients or reaction conditions used herein are to be understood as modified in all instances by the term "about".

An object of the present invention is to provide a method of producing and isolating monoalkylphosphates which, in particular, avoids the use of phosphorus oxychloride and the problems arising therefrom through the quantities of hydrogen chloride released. A further object of the invention is to separate the phosphoric acid formed during the reaction of an alcohol with polyphosphoric acid by a simple and inexpensive process.

Accordingly, fatty alcohols containing more than 8 carbon atoms are reacted with an excess of polyphosphoric acid, optionally in inert solvents. To split any polyphosphoric acid bonds (P-O-P) still present, the reaction mixture is first treated with a little water and, after removal of the solvent, is partially neutralized to a level of 60%, based on the acid number, with dilute alkali metal hydroxide, preferably NaOH. After a brief residence time at elevated temperature, the approximately 30% dispersion separates into two phases of which the upper, approximately 60% phase surprisingly contains all the monoalkylphosphate while the phosphoric acid is present almost completely in the lower phase.

Accordingly, the present invention relates to a process for the production and isolation of monoalkylphosphoric acid esters wherein (a) at least one saturated or olefinically unsaturated fatty alcohol or mixture of fatty alcohols containing from 8 to 18 carbon atoms, and preferably straight chain alcohols containing from 12 to 14 carbon atoms, is/are reacted with a 0.2 to 2-molar excess of polyphosphoric acid at a temperature of from 60° to 130° C., (b) following an after-reaction time of 120 to 300 minutes at a temperature of 90° to 130° C., the product of this reaction is slowly hydrolyzed at 90° to 100° C. with from 0.5 to 1.0 mole water, based on the quantity of phosphorus atoms in the reaction mixture, (c) the hydrolysis product is partially neutralized to a level of from 40 to 65%, and preferably to a level of from 50 to 60%, based on the acid number, with dilute alkali metal hydroxide, and (d) after a residence time of 30 to 180 minutes at a temperature of from 50° to 95° C., the two phases that result are separated from one another.

Fatty alcohols suitable for the purposes of the invention include octyl alcohol, nonyl alcohol, decyl alcohol, undecyl alcohol, dodecyl alcohol, tridecyl alcohol, tetradecyl alcohol, pentadecyl alcohol, hexadecyl alcohol, octadecyl alcohol, and octadecenyl alcohol.

According to the invention, the preferred alkali metal hydroxide is sodium hydroxide, which is used in solid form or preferably in the form of 10 to 60% by weight and more especially 30 to 50% by weight aqueous solutions.

In one embodiment of the invention, the reaction of the fatty alcohol with polyphosphoric acid can be carried out in an inert solvent selected from aromatics, alkanes, and cycloaolkanes with boiling points in the range of from 60° to 140° C.

In another embodiment of the invention, the unreacted alcohol can be removed from the solvent-free crude ester by steaming in vacuo at 0.1 to 20 mbar and at a temperature of 80° to 120° C.

Phosphating reactions with polyphosphoric acid, a highly viscous syrupy liquid, lead exclusively to monoesters. It does not matter whether the alcohol or the polyphosphoric acid (PPS) is added first for the reaction (Table 1); the composition of the resulting mixtures is almost identical.

Table 1

| Addition sequence | Molar ratio monoester: diester | Composition (% by weight) | | | | |
|---|---|---|---|---|---|---|
| | | mono-ester | di-ester | tri-ester | free $H_3PO_4$ | free alcohol |
| Alcohol added first | 49.0 | 49.8 | 1.6 | 4.4 | 8.6 | 35.6 |
| PPS added first | only mono-ester | 50.1 | — | 3.0 | 9.5 | 37.4 |

ROH/P = 1.5

Table 1-continued

| | Addition sequence | | | | |
|---|---|---|---|---|---|
| | Molar ratio monoester: diester | Composition (% by weight) | | | |
| | | mono-ester | di-ester | tri-ester | free H$_3$PO$_4$ | free alcohol |

| Alcohol: | n-octanol |
|---|---|
| Addition: | 50 to 70° C. |
| After-reaction: | 300 mins. at 95 to 105° C. |
| Hydrolysis: | 180 mins. at 100° C. |

Despite long reaction times and relatively high temperatures (up to 130° C.), large quantities of free alcohol or phosphoric acid are left, depending on the starting ratio (Table 2). The hydrolysis of the P—O—P bonds is of the upmost importance for reliable analysis of the reaction products. The treatment with water using at least 0.5 mole/P should be carried out over a period of 3 h at 90° to 100° C. Where the ratio of ROH to P is low, it is advisable to extend the treatment time to 5 hours.

TABLE 2

Starting ratio and various alcohols

| Example | ROH:P | Molar ratio mono: diester | Composition (% by weight) | | | | |
|---|---|---|---|---|---|---|---|
| | | | mono-ester | di-ester | tri-ester | free P$_3$PO$_4$ | free alcohol |
| 1 | 0.93 | only mono | 66.6 | — | 5.5 | 11.0 | 16.9 |
| 2 | 0.73 | only mono | 73.9 | — | 5.8 | 16.6 | 4.0 |
| 3 | 0.93 | only mono | 59.1 | — | 5.8 | 21.2 | 13.9 |
| 4 | 1.50 | 49 | 49.8 | 1.6 | 4.4 | 8.6 | 35.6 |

A C$_{12}$–C$_{14}$ lauryl alcohol containing approximately 70% dodecanol and approximately 30% tetradecanol was used as the alcohol in Examples 1 and 2.

n-Octanol was used as the alcohol in Examples 3 and 4.

Providing the quantities are not too large, the free alcohol can be removed by steaming in vacuo at 110° to 120° C.

The removal of the phosphoric acid is more of a problem. Washing methods of the type typically used in preparative chemistry almost always give dispersions which do not separate completely and which remain stable, even when salts and/or solvents are added. Surprisingly, quantititive separation was obtained in the case of the lauryl-myristyl alcohol ester. To this end, a 30% aqueous dispersion was partially neutralized (approx. 60%, based on the acid number) with sodium hydroxide.

After a brief residence time at 80° C., an almost clear lower phase was separated off, almost quantitatively containing all the inorganic phosphate, whereas only traces of inorganic phosphate could be detected in the upper, approximately 60% phase.

The invention is illustrated but not limited by the following Examples.

EXAMPLE 1

582 g (3.0 moles) of a mixture of lauryl and myristyl alcohol (OH number 289.2) and 200 ml toluene were introduced into a stirring apparatus equipped with a thermometer and reflux condenser. 345 g of a polyphosphoric acid (containing by calculation 84.5% phosphorus pentoxide) heated to 60° C. were added over a period of 15 minutes at a temperature of 80° C. through a heatable dropping funnel. After the mixture had been stirred for 3 h at 90° C., 82 g water were added to hydrolyze P—O—P bonds and stirring continued for another 5 h at 90° C. The apparatus was then modified by attachment of a water separator and 54 g water removed from the product while boiling under reflux.

After removal of the toluene by distillation under a pressure of 20 mbar and at a temperature of 110° C., the pressure was reduced to 5 mbar and the unreacted alcohol removed by steaming at the same temperature.

913.5 g of a product which solidified on cooling were obtained, of which the composition as determined by potentiometric multistage titration was as follows:

81.8 % monoalkyl ester
4.0 % dialkyl ester
15.2 % o-phosphoric acid

The acid number was 466.4.

To separate the phosphoric acid, 370 g of the crude ester were partially neutralized to a level of 60% with 148 g 50% sodium hydroxide after dilution beforehand with 851 g water. The mixture was transferred to a heatable separation funnel and kept at 80° C. for 1 hour. The phases formed were separated and analyzed.

The upper, milky-disperse phase (602 g) contained
36.9 % water
0.36 % inorganically and
5.52 % organically bound phosphorus.
The lower, slightly cloudly phase (766 g) contained
88.4 % water
2.0 % inorganically and
0.16 % organically bound phosphorus.

EXAMPLE 2

200 g of the crude ester obtained in accordance with Example 1 were mixed with 462 g water and partially neutralized to a level of 50% with 66.5 g 50% sodium hydroxide solution. After a residence time of 1 hour at 65° C., the phases formed were separated and analyzed.

The upper phase (432 g), which was milky-disperse after cooling, contained
0.16 % inorganically and
3.59 % organically bound phosphorus.
The lower, cloudy phase (252 g) contained
2.28 % inorganically
0.17 % organically bound phosphorus.

EXAMPLE 3

398.8 g (1.5 moles) of an oleyl-cetyl alcohol mixture (OH number 211, iodine number 55), 172.2 g polyphosphoric acid, 150 ml toluene and 41.0 g water were reacted to form the monoalkylphosphate by the method described in Example 1. The yield comprised 586 g; analysis revealed the following composition:

81.0 % monoalkylphosphate
8.4 % dialkylphosphate
10.6 % o-phosphoric acid.

The acid number was 345.9.

200 g of the crude ester were mixed with 462 g water and partially neutralized to a level of 60% with 59.2 g 50% sodium hydroxide solution, left standing for 2 hours at 65° C. and the phases formed subsequently separated.

Analysis produced the following result:

The upper phase (404.8 g), which became pasty after cooling, contained
1.07 % inorganically and
3.3 % organically bound phosphorus.
The lower, slightly cloudy phase (220 g) contained
2.23 % inorganically and
0.07 % organically bound phosphorus.

EXAMPLE 4

390 g (1.5 moles) tallow alcohol (OH number 215.8), 172.2 g polyphosphoric acid, 150 ml toluene and 41.0 ml water were reacted to form the monoalkylphosphate by the method described in Example 1. The yield comprised 560.7 g; analysis revealed the following composition:

78.7 % monoalkylphosphate
9.0 % dialkyl ester
12.3 % o-phosphoric acid.

The acid number was 365.9.

200 g of the crude ester were mixed with 462 g water and partially neutralized to a level of 60% with 62.8 g 50% sodium hydroxide solution, left standing for 2 h at 65° C. and the phases formed subsequently separated.

Analysis produced the following result:
The upper paste-like phase (392.5 g) contained
0.80 % inorganically and
3.61 % organically bound phosphorus.
The lower, almost clear phase (211 g) contained
2.08 % inorganically and
0.13 % organically bound phosphorus.

COMPARISION EXAMPLE 200 g of the crude ester obtained in accordance with Example 1 were mixed with 460 g water and partially neutralized to a level of 70% with 93 g 50% sodium hydroxide solution. After a residence time of 1 hour at 65° C., the phases formed, which were difficult to distinguish, were separated and analyzed.

The upper phase (163.6 g), which became pasty after cooling, contained
1.08 % inorganically and
4.52 % organically bound phosphorus.
The lower, milky-disperse phase (543 g) contained
1.62 % inorganically and
1.22 % organically bound phosphorus.

For 70% neutralization, therefore, the separation effect is only moderate.

We claim:

1. A process for the production and isolation of monoalkylphosphoric acid esters, comprising the steps of
    (a) reacting at least one fatty alcohol containing from 8 to 18 carbon atoms with from an about 0.2 to an about 2 molar excess of polyphosphoric acid in an inert solvent having a boiling point in the range of from about 60 to about 140° C. selected from the group consisting of alkanes, aromatics, and cycloalkanes at a temperature of from about 60° to about 130° C.;
    (b) maintaining the resulting reaction mixture at a temperature of from about 90° to about 130° C. for a period of time of from about 120 to about 300 minutes;
    (c) hydrolyzing the reaction mixture with from about 0.5 to about 1.0 mole of water, based on the quantity of phosphorus atoms in the reaction mixture, at a temperature of from about 90° to about 100° C. to form a hydrolysis product;
    (d) neutralizing from about 40 to about 65%, based on acid number, of the hydrolysis product with an alkali metal hydroxide;
    (e) maintaining the resulting mixture containing the partially neutralized hydrolysis product for a period of from about 30 to about 180 minutes at a temperature of from about 50° to about 95° C. to form two phases; and
    (f) separating the resulting phases.

2. The process of claim 1 wherein in step (a) the at least one fatty alcohol is a straight chain alcohol containing from 12 to 14 carbon atoms.

3. The process of claim 1 wherein in step (a) the at least one fatty alcohol is selected from the group consisting of octyl alcohol, nonyl alcohol, decyl alcohol, undecyl alcohol, dodecyl alcohol, tridecyl alcohol, tetradecyl alcohol, pentadecyl alcohol, hexadecyl alcohol, octadecyl alcohol and octadecenyl alcohol.

4. The process of claim 1 wherein in step (d) the percent neutralization is from about 50 to about 60%.

5. The process of claim 1 wherein in step (d) the alkali metal hydroxide is from about 10 to about 60% by weight NaOH solution.

6. The process of claim 5 wherein in step (d) from about 30 to about 50% by weight NaOH solution is employed.

7. The process of claim 1 wherein in step (d) solid NaOH is employed.

8. The process of claim 1 wherein prior to step (d) unreacted fatty alcohol is removed from the reaction mixture by the use of steam at a temperature of from about 80° to about 120° C. and a pressure of from about 0.1 to about 20 mbar.

9. The process of claim 1 wherein prior to step (d) both the solvent and unreacted fatty alcohol are removed from the reaction mixture from step (c).

10. The process of claim 1 wherein in step (a) the at least one fatty alcohol is a saturated alcohol.

* * * * *